United States Patent
Bolz

(10) Patent No.: US 6,868,713 B2
(45) Date of Patent: Mar. 22, 2005

(54) DEVICE FOR DETERMINING THE INTERNAL RESISTANCE OF A LINEAR OXYGEN PROBE

(75) Inventor: Stephan Bolz, Pfatter (DE)

(73) Assignee: Siemens Aktiengesellschaft, Munich (DE)

( * ) Notice: Subject to any disclaimer, the term of this patent is extended or adjusted under 35 U.S.C. 154(b) by 27 days.

(21) Appl. No.: 10/616,346

(22) Filed: Jul. 9, 2003

(65) Prior Publication Data

US 2004/0007045 A1 Jan. 15, 2004

Related U.S. Application Data

(63) Continuation of application No. PCT/DE02/00081, filed on Jan. 14, 2002.

(30) Foreign Application Priority Data

Jan. 16, 2001 (DE) .......................................... 101 01 755

(51) Int. Cl.⁷ ............................................... G01N 7/00
(52) U.S. Cl. ..................................... 73/23.31; 73/23.32
(58) Field of Search ............................ 73/23.21, 23.32; 123/703, 704; 204/406, 408; 205/783.5, 784, 784.5, 785, 785.5, 786; 324/442

(56) References Cited

U.S. PATENT DOCUMENTS

| | | | | |
|---|---|---|---|---|
| 4,028,207 A | * | 6/1977 | Faktor et al. ................ | 204/406 |
| 4,115,230 A | * | 9/1978 | Beckman ..................... | 204/431 |
| 4,135,381 A | | 1/1979 | Sherwin ......................... | 73/23 |
| 4,161,162 A | * | 7/1979 | Latsch et al. ................ | 123/435 |
| 4,472,262 A | | 9/1984 | Kondo et al. ................ | 204/408 |
| 4,779,078 A | * | 10/1988 | Ciolli .......................... | 340/634 |
| 5,106,481 A | | 4/1992 | Rankin et al. ............... | 204/426 |
| 5,725,425 A | * | 3/1998 | Rump et al. .................. | 454/75 |
| 5,980,728 A | * | 11/1999 | Farber et al. ................ | 205/784 |

FOREIGN PATENT DOCUMENTS

| | | | | |
|---|---|---|---|---|
| DE | 31 17 790 A1 | 11/1982 | ............ | G01K/7/26 |
| DE | 36 43 945 A1 | 6/1988 | ............ | G05B/23/02 |
| DE | 197 08 011 A1 | 9/1997 | ......... | G01N/27/416 |
| DE | 196 36 226 A1 | 3/1998 | ............ | F02D/41/14 |
| EP | 0 664 888 B1 | 9/1993 | ............ | G01R/27/14 |

* cited by examiner

*Primary Examiner*—C D Garber
(74) *Attorney, Agent, or Firm*—Baker Botts L.L.P.

(57) ABSTRACT

The device comprises a voltage divider (Rv1, Rv2) to whose two terminals the oscillator signal with a phase position that is mutually opposed is supplied until, in the instance of a switched-on probe heating, the voltage (VRpvs) that is proportional to the probe internal resistance (Rpvs) falls below a predetermined set value (set), whereby, at this point in time, the output signal of the oscillator (SZ) is supplied to both terminals of the voltage divider (Rv1, Rv2) with the same phase position (area 1) thus effecting an amplitude change-over (amplitude amplification).

13 Claims, 3 Drawing Sheets

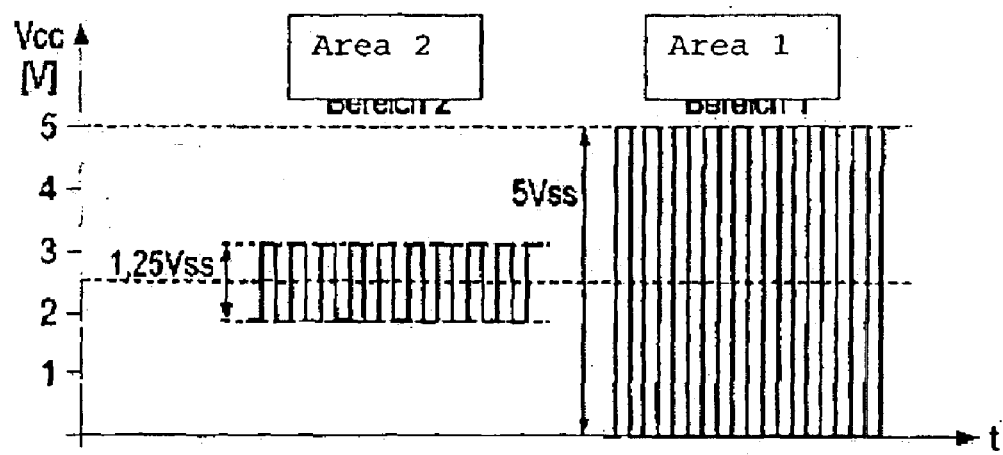
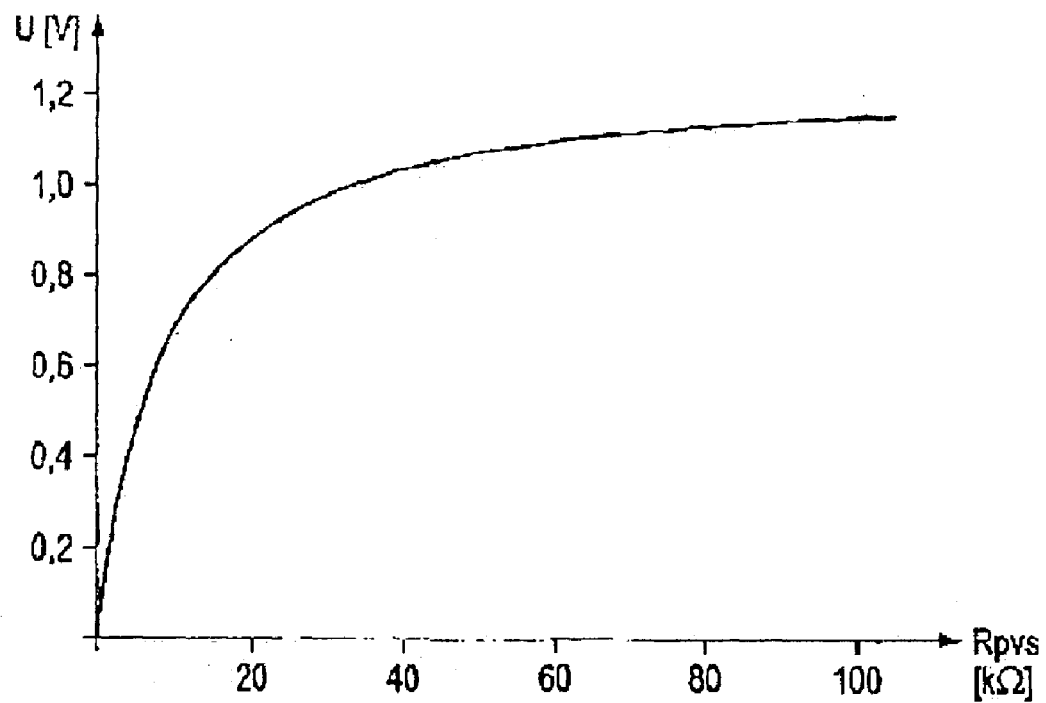

US 6,868,713 B2

DEVICE FOR DETERMINING THE INTERNAL RESISTANCE OF A LINEAR OXYGEN PROBE

CROSS REFERENCE TO RELATED APPLICATION

This application is a continuation of copending International Application No. PCT/DE02/00081 filed Jan. 14, 2002 and claiming a priority date of Jan. 16, 2001, which designates the United States.

TECHNICAL FIELD OF THE INVENTION

The invention relates to a device for determining the internal resistance of a linear oxygen probe (lambda probe) of an internal combustion engine.

BACKGROUND OF THE INVENTION

The dynamic resistance of the diffusion barrier of a linear lambda probe—which may be represented as a temperature-dependent, complex reactance with several RC sections—which is located in the exhaust gas conduit of an internal combustion engine for the purpose of determining the fuel/air mix supplied to the internal combustion engine, exhibits a temperature dependency that gives rise to errors in the transfer ratio, which is to say in the measurement result. This is countered by measuring the probe temperature and regulating it to a constant value (750° C., for example) by means of a heating element mounted in the lambda probe. A separate thermo element for measuring the temperature is dispensed with here for reasons of cost; the highly temperature-dependent internal resistance Rpvs of the lambda probe is measured instead.

A known method for determining the internal resistance of the Rpvs of a linear oxygen probe (lambda probe) is to cause an alternating current with, for example, 500 μApp (peak-peak) and a frequency of 3 kHz to impinge on the probe terminal Vs+. An alternating current signal drops on the internal resistor Rpvs. When Rpvs=100Ω: 500 μApp*100Ω=50 mVpp. This alternating current signal is amplified and rectified and can then be supplied to an analog/digital converter of a microprocessor in order to regulate the temperature of the oxygen probe.

The probe resistance Rpvs has a high impedance (around 1MΩ at 200° C.) during the heating phase and the amplitude of the alternating current signal dropping on it is correspondingly large (max. 5Vpp).

To allow the internal resistance Rpvs to be detected early, the amplifier (Rpvs_Amp) must have a low amplification. A typical measuring area would be 0 . . . 24*R0 (area 2: cold probe), where R0 corresponds to the nominal (set) probe resistance (100Ω at 750° C., for example). A wider measuring area spread is required in standard operation, 0 . . . 6*R0, for example (area 1: warm probe).

In known embodiments, the measuring areas are altered by changing over the amplification in the amplifier (Rpvs_Amp), for example *4 (heating phase, area 2) and *16 (standard operation, area 1). This converts the value for the probe internal resistance Rpvs (after amplification and rectification) into an output voltage in the area 0 . . . 4.8V. If an offset voltage of 0.1V is then added to this direct-current voltage, the result is an output voltage area of 0.1V . . . 4.9V. This voltage area can be processed in the rectifier (operating voltage 5V) and exploits the area of the analog/digital converter.

However, the large amplitude of the alternating current signal during the heating phase (max. 5Vpp) is a serious disadvantage of this solution. With some types of probe it can damage the ceramic (so-called blackening) so is not acceptable. A typical maximum value is approximately 2Vpp. The alternating current signal can accordingly only be applied when the probe is sufficiently warm—has low impedance.

In order nonetheless to be able to monitor the heating phase, recourse is taken to observing the pump current Ip (if the probe has sufficiently low impedance, a pump current Ip can also flow and Ip regulating stabilizes). However, this method is imprecise and requires considerable software expenditure in the microcontroller.

Another problem results from the fact that the oscillator has to be stopped when the circuit is switched into operation. Its output is applied to 0V or 5V. The probe terminal Vs+ which at this time has a very high impedance is connected to the oscillator output via resistor Rv and capacitor Cv. As capacitor Cv has been discharged, the potential on probe terminal Vs+ follows the potential of the oscillator output and is also applied to 0V or 5V.

However, this value is outside the nominal operating range. A diagnostic circuit, not represented here, detects this as a short-to-ground or short-to-battery voltage and would report it as a (non-existent) fault (phantom fault) requiring the aid of complex software measures to suppress.

SUMMARY OF THE INVENTION

The object of the invention is to provide a device for determining the internal resistance of a linear oxygen probe wherein the oscillator is also connected to the evaluation circuit during the heating phase and wherein the amplitude of the alternating current signal remains within its set area during this phase and supplies a measurement for the probe internal resistance.

This object can be achieved by a device for determining the internal resistance of a linear oxygen probe of an internal combustion engine, comprising an oscillator for producing an alternating current which is superimposed on the probe internal resistance through a decoupling capacitor via a probe terminal and which, after being amplified in an amplifier then rectified, generates a voltage proportional to the probe internal resistance as a regulating signal for a probe heater, and a voltage divider to whose two terminals the oscillator output signal is supplied which produces a voltage at its tap which generates the alternating current flowing through the probe internal resistor, wherein the output signal of the oscillator with a phase position that is mutually opposed is supplied to the two terminals of the voltage divider from the time the operating voltage is switched on, through which the oxygen probe is heated, until the voltage at the output of the amplifier that is proportional to the probe internal resistance falls below a pre-determined set value, and at this point in time the output signal of the oscillator is supplied to both terminals of the voltage divider with the same phase position.

The device may further comprise a first Exclusive-OR element whose input can be connected via a change-over switch to the high potential or low potential of an operating voltage, and whose other input is connected to the output of the oscillators, and a second Exclusive-OR element whose input is connected to the output of the oscillator and whose other input is connected to low potential, the output of the first Exclusive-OR element is connected to the output of the second Exclusive-OR element via the voltage divider formed by connecting a first resistor and second resistor in series, wherein the tap of the voltage divider, the junction of the two resistors, is connected to the probe terminal and the input of the amplifier via the decoupling capacitor. The device may further comprise a comparator to which the output voltage, a pre-determined set value, and an instruction are supplied, which connects input of the first Exclusive-OR element via the change-over switch to the high potential of the operating voltage, when the operating voltage is switched on at the start of operation and for as long as the output voltage exceeds the set value, and which applies input of the first Exclusive-OR element via the change-over switch to low potential of the operating voltage, as soon as the output voltage falls below the set value. The set value may be selected such that the output voltage is less than the high potential after the change-over switch has changed over from high potential to low potential.

The object can also be achieved by a device for determining the internal resistance of a linear oxygen probe of an internal combustion engine, comprising an oscillator generating an alternating current output signal, a controllable phase shifter for generating an in-phase oscillator output signal or an opposite phase oscillator output signal, a voltage divider receiving the oscillator output signal and the phase shifter output signal, a decoupling capacitor superimposing the divided output signal on a probe internal resistance, an amplifier coupled with the probe for amplifying the probe signal, a rectifier coupled with the amplifier for rectifying the amplified signal, and a comparator for comparing a voltage proportional to the probe internal resistance with a predetermined value to generate a control signal for the phase shifter.

The device may further comprise a first Exclusive-OR element whose input can be connected via a change-over switch to the high potential or low potential of an operating voltage, and whose other input is connected to the output of the oscillators, and a second Exclusive-OR element whose input is connected to the output of the oscillator and whose other input is connected to low potential, the output of the first Exclusive-OR element is connected to the output of the second Exclusive-OR element via the voltage divider formed by connecting a first resistor and second resistor in series, wherein the tap of the voltage divider, the junction of the two resistors, is connected to the probe terminal and the input of the amplifier via the decoupling capacitor. The device may further comprise a comparator to which the output voltage, a pre-determined set value, and an instruction are supplied, which connects input of the first Exclusive-OR element via the change-over switch to the high potential of the operating voltage, when the operating voltage is switched on at the start of operation and for as long as the output voltage exceeds the set value, and which applies input of the first Exclusive-OR element via the change-over switch to low potential of the operating voltage, as soon as the output voltage falls below the set value. The set value may be selected such that the output voltage is less than the high potential after the change-over switch has changed over from high potential to low potential. The controllable phase shifter may comprise an EXOR gate receiving the oscillator output signal and a logical signal as a control signal.

The object may also be achieved by a method for operating a linear oxygen probe of an internal combustion engine, comprising the steps of:
generating a first and second alternating current wherein the second alternating current is either in-phase or opposite phase to the first alternating current,
combining the first and second alternating currents by means of a voltage divider,
superimposing the combined signal on the probe internal resistance,
amplifying and rectifying a probe signal;
comparing the probe amplified and rectified signal with a threshold value;
depending on the comparison switching the second alternating current to be in-phase or opposite phase.

The step of superimposing can be performed by means of a capacitor. The switching may be performed by means of a logic signal. The threshold value can be selected such that the output voltage is less than the high potential of the logic signal after the change-over switch has changed over from high potential to low potential.

BRIEF DESCRIPTION OF THE DRAWINGS

An embodiment of the invention is explained in greater detail below with the aid of a schematic.

FIG. 3 shows the oscillator output signals of the device according to the invention, FIG. 4 shows the output signal VRpvs as a function of the probe internal resistance Rpvs.

DETAILED DESCRIPTION OF THE PREFERRED EMBODIMENTS

Figure 1:
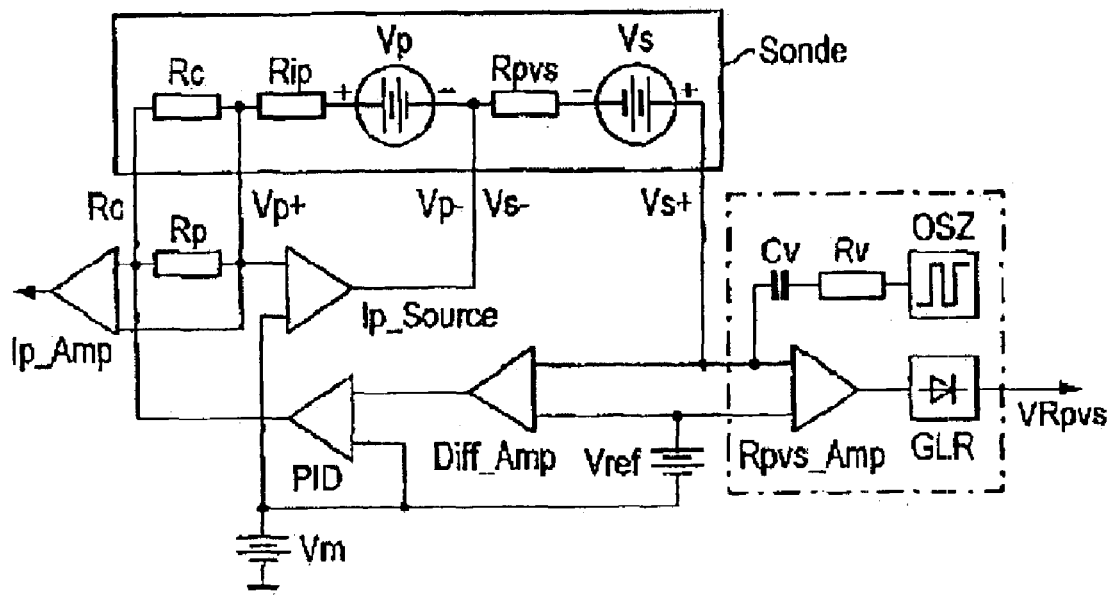
FIG. 1 shows a known device for operating a linear lambda probe with a known device for determining the probe internal resistance Rpvs.

FIG. 1 shows a device known per se for operating a linear lambda probe with a known device for determining the probe internal resistance.
Located top left is the probe with
the calibration resistor Rc (terminals Rc, Vp+),
the pump cell (terminals Vp+, Vp−) with the substitute resistor Rip and polarizing voltage Vp, and
the measuring cell (terminals Vs+, Vs−) with Nernst voltage Vs and probe internal resistance Rpvs.
Beneath the probe is a known evaluation circuit (Ip regulator) with a
differential amplifier (Diff_Amp),
reference voltage source (Vref),
AGC amplifier (PID),
mid-voltage source (Vm),
pump current source (Ip source), and
parallel resistor Rp.

Shown on the right of the probe and evaluation circuit, framed by a dashed border, is a known device for measuring the probe internal resistance Rpvs with an oscillator OSZ, a resistor Rv, a decoupling capacitor Cv, and an amplifier Rpvs_Amp and rectifier GLR.

The principle of the lambda probe and its evaluation circuit is known and will not be further elucidated.

To measure the probe internal resistance Rpvs, a measuring signal produced in the oscillator OSZ, for example a rectangular alternating current with 500 $\mu$App (peak-peak) and a frequency of 3 kHz, is applied to the probe. The signal is supplied to the first terminal Vs+ of the lambda probe via the high-impedance resistor Rv and decoupling capacitor Cv. A square-wave voltage of 500 $\mu$App*100$\Omega$, =50 mVpp then appears on the internal resistance Rpvs, which can be assumed at that instance to be, for example, 100Ω. This square-wave voltage is amplified in an amplifier Rpvs_Amp and rectified in a rectifier GLR; it can then be supplied in the form of a direct-current voltage VRpvs to a microprocessor, which is not represented, as a regulating signal for regulating the temperature of the lambda probe. The disadvantages of this circuit have been presented above.

Figure 2:
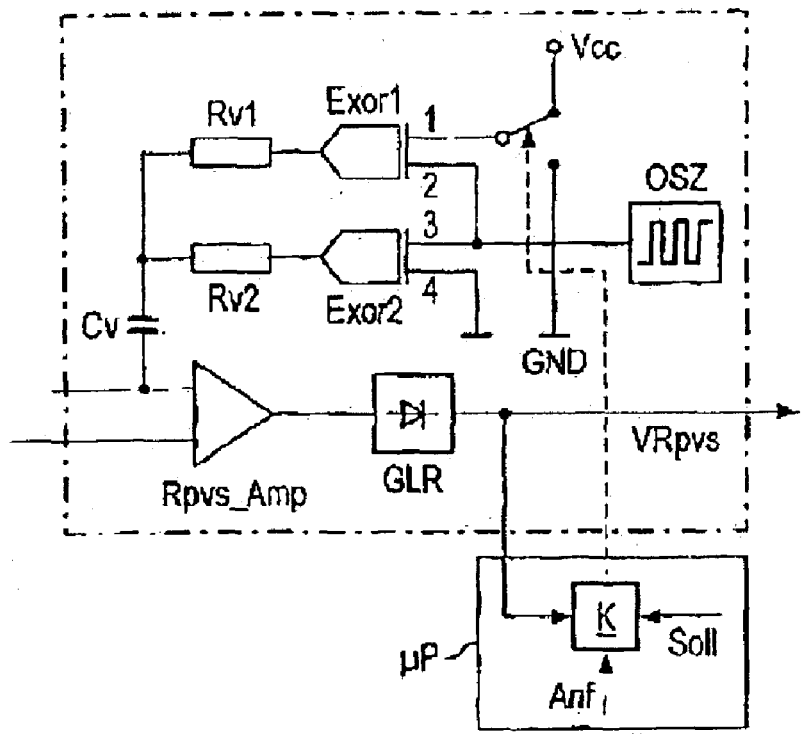
FIG. 2 shows a device according to the invention for determining the probe internal resistance Rpvs.

FIG. 2 shows, framed by a dashed border, the circuit of a device according to the invention for determining, the probe internal resistance Rpvs. This circuit again contains the oscillator OSZ, the amplifier Rpvs_Amp, the rectifier GLR, and the decoupling capacitor Cv from FIG. 1.

The resistor Rv has been replaced by two resistors Rv1 and Rv2; two Exor elements Exor1 and Exor2 (exclusive-OR elements, of type 74HC86, for instance) and a change-over switch S are provided in addition.

The output of the oscillator OSZ, whose output signal is to be superimposed as a square-wave current on the probe internal resistance Rpvs, is connected to input 2 of Exor1 and input 3 of Exor2. Input 4 of Exor2 is applied to low potential (reference potential GND), and input 1 of Exor1 can be applied to low potential (GND) or to high potential (operating voltage potential Vcc=5V) via the change-over switch S.

The output of Exor1 is connected via a resistor Rv1 to the decoupling capacitor Cv and the output of Exor2 is connected via a resistor Rv2 to the decoupling capacitor Cv, which is connected in the familiar manner to the probe internal resistor Rpvs and leads on to the amplifier Rpvs_Amp and, further on, to the rectifier GLR.

The resistors Rv1 and Rv2 are specified as follows:

$Rv1=Z/\{0.5*(1-N)\}$, (=26.67 kΩ), $Rv2=Z/\{0.5*(1+N)\}$, (=16.00 kΩ), with
N=Area 1/area 2 voltage ratio (e.g.: 0.25),
Z=Total resistance: Rv1 parallel to Rv2 (e.g.: 10 kΩ).
The device operates as follows:

When the operating voltage Vcc=5V is switched on, the probe heater is first activated and area 2 is selected because Rpvs>100 kΩ in the cold condition. Input 1 of Exor1 is applied to high potential=5V. Exor1 operates as an inverter, Exor2 as a non-inverting buffer; Exor1 and Exor2 operate in mutual phase opposition. The 3-kHz square-wave signal appears at their outputs with opposing phase position, i.e. output Exor1=Low (0V), output Exor2=High (+5V), or vice versa.

Resistors Rv1 and Rv2 in this case form a voltage divider with an internal resistance of 10 kΩ. At the junction of Rv1 and Rv2 there is an alternating current which—depending on the resistance divider ratio—is either Vcc[Rv1/(Rv1+Rv2)]=1.87V or Vcc[Rv2/(Rv1+Rv2)]=3.13V=1.25Vpp (see FIG. 3: area 2). The alternating current flowing into the probe internal resistor Rpvs is determined analogously.

The output alternating voltage at the junction of the two resistors Rv1 and Rv2, which is to say at the voltage divider tap, is between, for example, 3.13V and 1.87V=1.25Vpp in no-load operation or, depending on the value of Rpvs—as a function of its temperature—correspondingly lower.

This value is supplied to the input of the amplifier Rpvs_Amp via the decoupling capacitor Cv. This prevents false fault detection of the circuit.

If the probe internal resistance Rpvs in area 2 falls below a pre-determined value, for example to 600Ω (or if the output signal VRpvs drops to a corresponding voltage value), input 1 of Exor1 is switched over from high to low potential via change-over switch S, and thus to area 1, which is to say the amplification is increased by the factor 4.

Low potential GND=0V is now being applied to input 1 of Exor1. Exor1 and Exor2 both operate as non-inverting buffers in co-phasal mode, which is to say the 3-kHz square-wave signal (in no-load operation 5Vpp) appears at their outputs with the same phase position: both simultaneously connected to either low or high potential. The resistors Rv1 and Rv2 appear connected in parallel, Rv1=16 kΩ, Rv2=26,67 KΩ, the common resistance Rv∥Rv2=10 kΩ. An alternating current of 5Vpp/10 kΩ=500 μApp correspondingly flows through them into the probe resistance Rpvs. The result is an alternating current of 5Vpp (FIG. 3: area 1).

With the decoupling capacitor Cv inserted to decouple the direct-current voltage, an alternating current source is being applied to the probe internal resistor with an internal resistance of 10 kΩ and a no-load voltage of 1.25Vpp (area 2) or 5Vpp (area 1).

The change-over switch S is changed over by a comparator K, which in area 2 compares the output voltage VRpvs with a pre-determined set value. Output 1 continues being applied to high potential while VRpvs>the set value; if VRpvs<the set value, output 1 is switched over to low potential (area 1). It then maintains this position, with the probe internal resistance Rpvs being regulated to 100Ω/750° C. via the output signal VRpvs until the operating voltage is disconnected.

The comparator K is part of an integrated circuit, a microprocessor μP, for example, symbolized by a frame. The device within the dashed border can also be at least partially integrated in this integrated circuit, as can the entire evaluation circuit shown in FIG. 1. When the operating voltage is switched on (start of operation), the comparator is set by means of an instruction Anf in such a way that the change-over switch S connects input 1 of Exor1 to high potential (area 2).

FIG. 3 shows the oscillator output signals in areas 1 (5Vpp) and 2 (1.25Vpp).

FIG. 4 shows the signal amplitude of the voltage dropping on the probe internal resistor or at the input of the amplifier Rpvs_Amp as a function of the probe internal resistance Rpvs. This has a value>>100 kΩ at a temperature T=20° C. and around 100 kΩ at T=200° C. (right-hand side of the diagram); a voltage of around 1.16Vpp, max. 1.25Vpp, is then being applied to the amplifier input.

If the probe internal resistance Rpvs is at its nominal value of 100Ω at T=750° C., where temperature regulation takes place (left-hand side of the diagram near the zero point), a voltage of around 0.35Vpp will be present at the amplifier input. The temperature T increases as the resistance value decreases, so from right to left on the abscissa.

Figure 5:
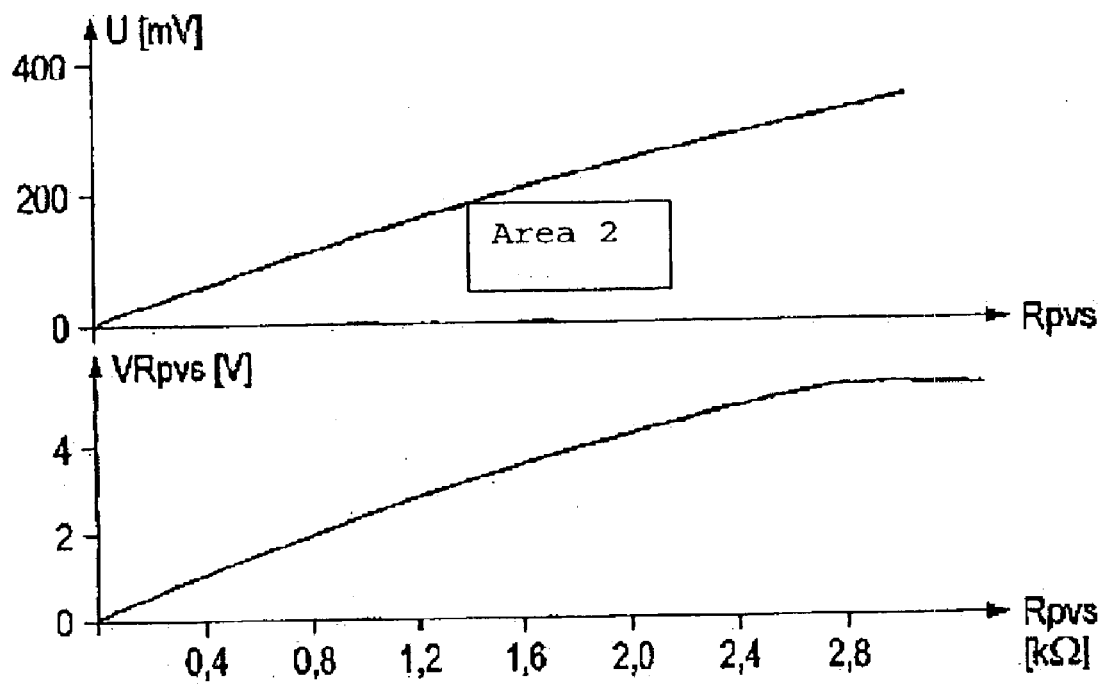
FIG. 5 shows the output signal VRpvs and voltage on the probe in the amplification area 2 (heating phase)

FIG. 5 shows the signal amplitudes on probe internal resistor Rpvs or on the input of the amplifier Rpvs_Amp (top) and, below that, the direct-current voltage VRpvs that can be tapped at the output of the rectifier GLR, each in area 2, see FIG. 4. Proceeding from an operating start with a probe temperature T=20° C. and Rpvs>>100 kΩ, the amplifier output is initially in a saturated state and the probe is heated and accordingly heats up. If the probe internal resistance Rpvs<2.4 kΩ (top), the output voltage VRpvs (bottom) will decrease. If Rpvs≦600Ω, change-over to area 1 takes place, see FIG. 6.

Figure 6:
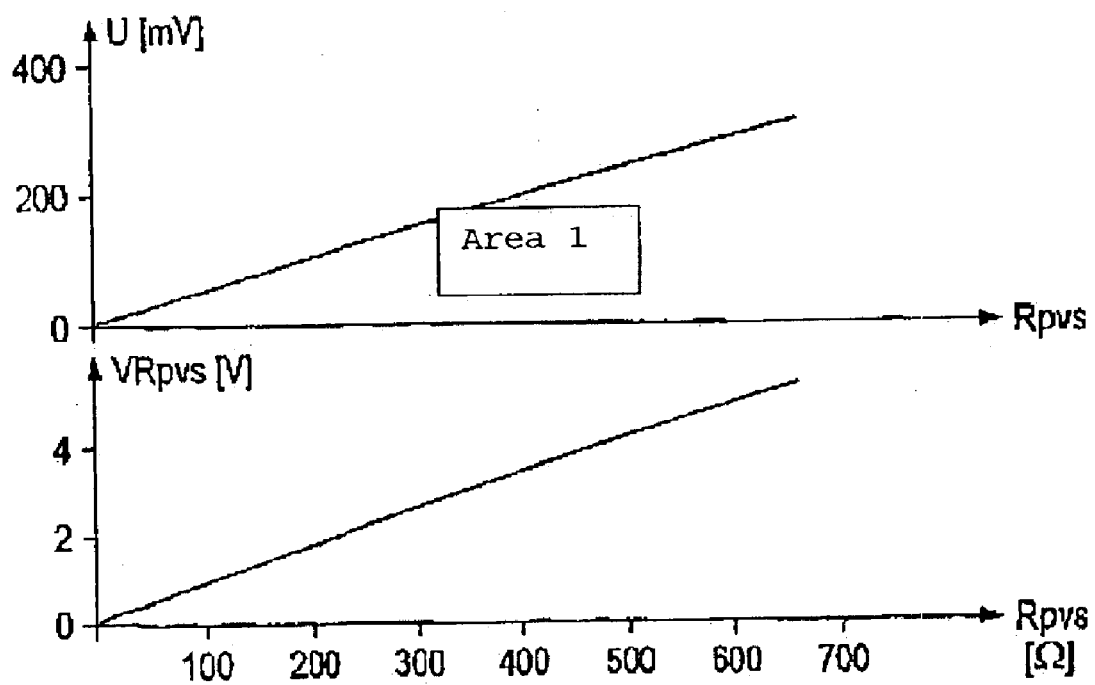
FIG. 6 shows the output signal VRpvs and voltage on the probe in the amplification area 1 (standard operation).

FIG. 6 shows, at top, the signal amplitude on the sensor and; below that, the direct-current voltage VRpvs that can be tapped at the output in area 1, the actual regulating area for probe heating in order to regulate the probe internal resistance to Rpvs=100Ω.

The circuit according to the invention has the following advantages:

Change-over of amplification for areas 1 and 2 is done by changing over the amplitude of the alternating current signal:

Area 1: 0 . . . 6R0 (standard operation); Amplitude=SVpp.

Area 2: 0 . . . 24R0 (start-up of probe); Amplitude=SVpp/4=3.12V–1.87V=±0.625V=1.25Vpp, see FIG. 3 (R0= Rpvs at 750° C.=100Ω).

The areas are very easy to define by means of two resistors.

The source resistance is always constant, independently of the area.

The circuit is easy to integrate or can be manufactured using standard components.

The maximum permissible probe voltage of ±2V (4Vpp) with a cold probe is no longer exceeded.

What is claimed is:

1. Device for determining the internal resistance of a linear oxygen probe of an internal combustion engine, comprising:

an oscillator for producing an alternating current which is superimposed on the probe internal resistance through a decoupling capacitor via a probe terminal and which, after being amplified in an amplifier then rectified, generates a voltage proportional to the probe internal resistance as a regulating signal for a probe heater, and a voltage divider to whose two terminals the oscillator output signal is supplied which produces a voltage at its tap which generates the alternating current flowing through the probe internal resistor, wherein the output signal of the oscillator with a phase position that is mutually opposed is supplied to the two terminals of the voltage divider from the time the operating voltage is switched on, through which the oxygen probe is heated, until the voltage at the output of the amplifier that is proportional to the probe internal resistance falls below a pre-determined set value, and at this point in time the output signal of the oscillator is supplied to both terminals of the voltage divider with the same phase position.

2. Device according to claim 1, further comprising a first Exclusive-OR element whose input can be connected via a change-over switch to the high potential or low potential of an operating voltage, and whose other input is connected to the output of the oscillators, a second Exclusive-OR element whose input is connected to the output of the oscillator and whose other input is connected to low potential, the output of the first Exclusive-OR element is connected to the output of the second Exclusive-OR element via the voltage divider formed by connecting a first resistor and second resistor in series, and wherein the tap of the voltage divider, the junction of the two resistors, is connected to the probe terminal and the input of the amplifier via the decoupling capacitor.

3. Device according to claim 1, further comprising a comparator to which the output voltage, a pre-determined set value, and an instruction are supplied, which connects input of the first Exclusive-OR element via the change-over switch to the high potential of the operating voltage, when the operating voltage is switched on at the start of operation and for as long as the output voltage exceeds the set value, and which applies input of the first Exclusive-OR element via the change-over switch to low potential of the operating voltage, as soon as the output voltage falls below the set value.

4. Device according to claim 3, wherein the set value is selected such that the output voltage is less than the high potential after the change-over switch has changed over from high potential to low potential.

5. Device for determining the internal resistance of a linear oxygen probe of an internal combustion engine, comprising:

an oscillator generating an alternating current output signal, a controllable phase shifter for generating an in-phase oscillator output signal or an opposite phase oscillator output signal, a voltage divider receiving the oscillator output signal and the phase shifter output signal, a decoupling capacitor superimposing the divided output signal on a probe internal resistance, an amplifier coupled with the probe for amplifying the probe signal, a rectifier coupled with the amplifier for rectifying the amplified signal, and a comparator for comparing a voltage proportional to the probe internal resistance with a predetermined value to generate a control signal for the phase shifter.

6. Device according to claim 5, further comprising a first Exclusive-OR element whose input can be connected via a change-over switch to the high potential or low potential of an operating voltage, and whose other input is connected to the output of the oscillators, a second Exclusive-OR element whose input is connected to the output of the oscillator and whose other input is connected to low potential, the output of the first Exclusive-OR element is connected to the output of the second Exclusive-OR element via the voltage divider formed by connecting a first resistor and second resistor in series, and wherein the tap of the voltage divider, the junction of the two resistors, is connected to the probe terminal and the input of the amplifier via the decoupling capacitor.

7. Device according to claim 5, further comprising a comparator to which the output voltage, a pre-determined set value, and an instruction are supplied, which connects input of the first Exclusive-OR element via the change-over switch to the high potential of the operating voltage, when the operating voltage is switched on at the start of operation and for as long as the output voltage exceeds the set value, and which applies input of the first Exclusive-OR element via the change-over switch to low potential of the operating voltage, as soon as the output voltage falls below the set value.

8. Device according to claim 7, wherein the set value is selected such that the output voltage is less than the high potential after the change-over switch has changed over from high potential to low potential.

9. Device according to claim 5, wherein the controllable phase shifter comprises an EXOR gate receiving the oscillator output signal and a logical signal as a control signal.

10. Method for operating a linear oxygen probe of an internal combustion engine, comprising the steps of:

generating a first and second alternating current wherein the second alternating current is either in-phase or opposite phase to the first alternating current;

combining the first and second alternating currents by means of a voltage divider;

superimposing the combined signal on the probe internal resistance;

amplifying and rectifying a probe signal;

comparing the probe amplified and rectified signal with a threshold value; and depending on the comparison switching the second alternating current to be in-phase or opposite phase.

11. The method as in claim 10, wherein the step of superimposing is performed by means of a capacitor.

12. The method as in claim 10, wherein the switching is performed by means of a logic signal.

13. The method as in claim 12, wherein the threshold value is selected such that the output voltage is less than the high potential of the logic signal after the change-over switch has changed over from high potential to low potential.

* * * * *